(12) United States Patent
Peng et al.

(10) Patent No.: US 10,620,287 B2
(45) Date of Patent: Apr. 14, 2020

(54) METHOD AND APPARATUS FOR DENOISING MAGNETIC RESONANCE DIFFUSION TENSOR, AND COMPUTER PROGRAM PRODUCT

(71) Applicant: SHENZHEN INSTITUTES OF ADVANCED TECHNOLOGY CHINESE ACADEMY OF SCIENCES, Shenzhen, Guangdong (CN)

(72) Inventors: Xi Peng, Guangdong (CN); Dong Liang, Guangdong (CN); Xin Liu, Guangdong (CN); Hairong Zheng, Guangdong (CN)

(73) Assignee: SHENZHEN INSTITUTES OF ADVANCED TECHNOLOGY CHINESE ACADEMY OF SCIENCES, Shenzhen (CN)

( * ) Notice: Subject to any disclaimer, the term of this patent is extended or adjusted under 35 U.S.C. 154(b) by 355 days.

(21) Appl. No.: 15/618,979

(22) Filed: Jun. 9, 2017

(65) Prior Publication Data

US 2017/0363702 A1     Dec. 21, 2017

Related U.S. Application Data

(63) Continuation of application No. PCT/CN2014/095362, filed on Dec. 29, 2014.

(30) Foreign Application Priority Data

Dec. 11, 2014  (CN) .......................... 2014 1 0758290

(51) Int. Cl.
*G01R 33/563* (2006.01)
*A61B 5/055* (2006.01)
(Continued)

(52) U.S. Cl.
CPC ........ *G01R 33/56341* (2013.01); *A61B 5/055* (2013.01); *G01R 33/5602* (2013.01);
(Continued)

(58) Field of Classification Search
CPC .. A61B 5/055; A61B 5/7203; G01R 33/5602; G01R 33/56341; G06T 5/002; G06T 2207/10092
See application file for complete search history.

(56) References Cited

U.S. PATENT DOCUMENTS 7,630,530 B2 * 12/2009 McGraw ............... G06T 7/0012
                                                    382/128
7,889,899 B2 *  2/2011 Nadar .............. G01R 33/56341
                                                    324/307
(Continued)

FOREIGN PATENT DOCUMENTS

CN      102008307      4/2011
CN      102309328     10/2011
(Continued)

OTHER PUBLICATIONS

Majon et al., "Diffusion Weighted Image Denoising Using Overcomplete Local PCA", Sep. 3, 2013, PLoS ONE 8(9): e73021. doi:10.1371/journal.pone.0073021 (Year: 2013).*
(Continued)

*Primary Examiner* — Stephanie E Bloss
(74) *Attorney, Agent, or Firm* — Bayramoglu Law Offices LLC

(57) ABSTRACT

The application provides a method, apparatus and computer program product for denoising a magnetic resonance diffusion tensor, wherein the method comprises: collecting data of K space; calculating a maximum likelihood estimator of a diffusion tensor according to the collected data of K space; calculating a maximum posterior probability estimator of the
(Continued)

diffusion tensor by using sparsity of the diffusion tensor and sparsity of a diffusion parameter and taking the calculating maximum likelihood estimator as an initial value; and calculating the diffusion parameter according to the calculated maximum posterior probability estimator. The application solves the technical problem in the prior art of how to realize high precision denoising of diffusion tensor while not increasing scanning time and affecting spatial resolution, achieves the technical effects of effectively suppressing noises in the diffusion tensor and improving the estimation accuracy of the diffusion tensor.

10 Claims, 2 Drawing Sheets

(51) Int. Cl.
    *G01R 33/56*     (2006.01)
    *G06T 5/00*     (2006.01)
    *A61B 5/00*     (2006.01)

(52) U.S. Cl.
    CPC ............ *G06T 5/002* (2013.01); *A61B 5/7203* (2013.01); *G06T 2207/10092* (2013.01)

(56) References Cited

U.S. PATENT DOCUMENTS

| | | | |
|---|---|---|---|
| 2006/0165308 A1* | 7/2006 | Chakraborty | G06T 5/002 382/254 |
| 2008/0109171 A1* | 5/2008 | McGraw | G01R 33/56341 702/19 |
| 2009/0190815 A1* | 7/2009 | Dam | A61B 5/055 382/131 |
| 2009/0190816 A1 | 7/2009 | Yanasak et al. | |
| 2009/0290770 A1* | 11/2009 | Mori | A61B 5/055 382/128 |
| 2011/0282183 A1* | 11/2011 | Song | A61B 5/055 600/410 |
| 2014/0210474 A1* | 7/2014 | Haldar | G01R 33/56341 324/318 |
| 2014/0253118 A1* | 9/2014 | Koay | G01R 33/4826 324/309 |
| 2015/0022210 A1* | 1/2015 | Yokosawa | G01R 33/56341 324/318 |

FOREIGN PATENT DOCUMENTS

| | | |
|---|---|---|
| CN | 103705239 | 4/2014 |
| CN | 103985099 | 8/2014 |
| CN | 1632830 | 6/2015 |
| WO | 0185230 | 11/2001 |

OTHER PUBLICATIONS

Zhang et al, "Two-stage image denoising by principal component analysis with local pixel grouping", 2010, Pattern Recognition 43 (2010) 1531-1549 (Year: 2010).*

Hua et al, "Semiparametric Bayesian local functional models for diffusion tensor tract statistics", Jun. 23, 2012, NeuroImage 63 (2012) 460-474 (Year: 2012).*

First Chinese Office Action and Search Report, dated Oct. 28, 2016 in the corresponding Chinese patent application No. 201410758290. 6, 14 pages.

Peng et al., "Exploiting parameter sparsity in model-based reconstruction to accelerate proton density and T2 mapping", Medical Engineering & Physics, vol. 36, pp. 1428-1435, 2014.

International Search Report, issued in the corresponding PCT application No. PCT/CN2014/095362, dated Aug. 26, 2015, 6 pages.

* cited by examiner

METHOD AND APPARATUS FOR DENOISING MAGNETIC RESONANCE DIFFUSION TENSOR, AND COMPUTER PROGRAM PRODUCT

CROSS-REFERENCE TO RELATED APPLICATIONS

This application is a continuation application of international application No. PCT/CN2014/095362, filed on Dec. 29, 2014, which claims priority to Chinese Patent Application No. 201410758290.6, filed on Dec. 11, 2014, with the title "Method And Apparatus For Denoising A Magnetic Resonance Diffusion Tensor", both of which are hereby incorporated by reference in their entireties.

TECHNICAL FIELD

The present application relates to the technical field of magnetic resonance imaging (MRI), and more particularly, to a method, apparatus and computer program product for denoising a magnetic resonance diffusion tensor.

BACKGROUND

Magnetic Resonance Diffusion Tensor Imaging (abbreviated as DTI) utilizes the principle of anisotropy of free thermal motion of water molecules in tissues to explore microstructure of the tissues so as to achieve the purpose of studying functions of a human body.

Currently, DTI is the unique non-invasive imaging method by which fiber bundles of cerebral white matter can be displayed in vivo. However, signal-to-noise ratio (SNR) of DTI is relatively low, which greatly limits widespread applications of DTI in clinic.

The physical mechanism of Magnetic Resonance Diffusion Tensor Imaging can be represented as:

$$d = F\rho + n \quad \text{(Formula 1)}$$

wherein, d represents a signal collected by a magnetic resonance instrument, F represents Fourier coding matrix, ρ represents a diffusion weighted image, and n is generally assumed as complex gaussian white noise.

In DTI, the $m^{th}$ diffusion weighted image $\rho_m$ may be represented as:

$$\rho_m = I_0 e^{i\varphi_m} e^{-b g_m^T D g_m} \quad \text{(Formula 2)}$$

wherein, $I_0 \in R^{N \times 1}$ represents a non-diffusion-weighted reference image, $\varphi_m \in R^{N \times 1}$ represents a phase of the $m^{th}$ diffusion weighted image, b represents a diffusion weighted factor (constant), $g_m$ represents a diffusion gradient vector $g_m = (g_{xm}, g_{ym}, g_{zm})^T$ corresponding to the $m^{th}$ diffusion weighted image, D represents a diffusion tensor, and specifically D may be represented as:

$$D = \begin{pmatrix} D_1 & D_4 & D_5 \\ D_4 & D_2 & D_6 \\ D_5 & D_6 & D_3 \end{pmatrix} \quad \text{(Formula 3)}$$

wherein, each $D_i \in R^{N \times 1}$, and N represents the number of pixel points of a magnetic resonance image.

Specifically, the process of diffusion tensor imaging mainly includes the following steps:

Step 1: rebuilding the image ρ by the collected signal d;

Step 2: estimating a tensor matrix D corresponding to each spatial position according to a model tensor (i.e., the above Formula 2);

Step 3: calculating to obtain various diffusion parameters such as MD, FA, or the like from the tensor matrix D, according to the following Formulas 4 and 5:

$$MD = (\lambda_1 + \lambda_2 + \lambda_3)/3 \quad \text{(Formula 4)}$$

$$FA = \frac{1}{\sqrt{3[(\lambda_1 - MD)^2 + (\lambda_2 - MD)^2 + (\lambda_3 - MD)^2]/2(\lambda_1^2 + \lambda_2^2 + \lambda_3^2)}} \quad \text{(Formula 5)}$$

wherein, $\lambda_1$, $\lambda_2$, $\lambda_3$ are characteristic values of the matrix D.

In order to increase the SNR of DTI, currently there is a relatively direct method that is to take an average by sampling many times or to reduce the sampling area of K space, and this is called as the $1^{st}$ method.

Currently, there is still a common method for improving diffusion tensor imaging quality. This method includes: firstly rebuilding a diffusion weighted image after acquiring scanning data of K space; then denoising the image by using a method of signal processing; finally calculating a diffusion tensor and various diffusion parameters by the denoised image. That is, during the process, it is necessary to firstly rebuild the image and then denoise the image, which is called as the $2^{nd}$ method.

SUMMARY

The inventor of the present application found that, although the $1^{st}$ method may increase the SNR in practical applications, the method may increase scanning time or affect spatial resolution. And in the $2^{nd}$ method, system errors generated in the image denoising process may usually be transferred further to subsequent tensor calculation, consequently affecting the accuracy of the diffusion tensor.

There is currently no effective solution proposed yet aiming at the technical problem of how to realize high precision denoising of diffusion tensor while not increasing scanning time and affecting spatial resolution.

The embodiments of the present application provide a method for denoising a magnetic resonance diffusion tensor, so as to solve one or more technical problems in the prior art, the method includes:

collecting data of K space;

calculating a maximum likelihood estimator of a diffusion tensor according to the collected data of K space;

calculating a maximum posterior probability estimator of the diffusion tensor by using sparsity of the diffusion tensor and sparsity of a diffusion parameter and taking the calculated maximum likelihood estimator as an initial value; and calculating the diffusion parameter according to the calculated maximum posterior probability estimator.

In one embodiment, the calculating a maximum likelihood estimator of the diffusion tensor according to the collected data of K space includes:

calculating the maximum likelihood estimator of the diffusion tensor in accordance with the following formula:

$$\tilde{D} = \underset{D}{\operatorname{argmin}} \sum_m \left\| d_m - FI_0 e^{i\varphi_m} e^{-bg_m^T D g_m} \right\|_2^2 \quad \text{(Formula 6)}$$

wherein, $\tilde{D}$ represents the maximum likelihood estimator of the diffusion tensor, $d_m$ represents data of K space corresponding to the $m^{th}$ diffusion weighted image, F represents Fourier coding matrix, $I_0$ represents a non-diffusion-weighted reference image, $\varphi_m$ represents a phase of the $m^{th}$ diffusion weighted image, b represents a diffusion weighted factor, and $g_m = (g_{xm}, g_{ym}, g_{zm})^T$ represents a diffusion gradient vector corresponding to the $m^{th}$ diffusion weighted image.

In one embodiment, the calculating a maximum posterior probability estimator of the diffusion tensor by using sparsity of the diffusion tensor and sparsity of a diffusion parameter and taking the calculated maximum likelihood estimator as an initial value includes:

calculating the maximum posterior probability estimator of the diffusion tensor in accordance with the following formula:

$$\tilde{D} = \quad \text{(Formula 7)}$$
$$\underset{D}{\operatorname{argmin}} \sum_m \left\| d_m - F_m I_0 e^{i\varphi_m} e^{-bg_m^T D g_m} \right\|_2^2 + \gamma_1 R(D) + \gamma_2 G(FA)$$

wherein, $$FA = \frac{\sqrt{2}}{2} \sqrt{3 - \frac{(D_1 + D_2 + D_3)^2}{D_1^2 + D_2^2 + D_3^2 + 2D_4^2 + 2D_5^2 + 2D_6^2}},$$

R(•) represents a penalty function acting on the diffusion tensor D, G(•) represents a penalty function acting on a diffusion parameter FA, $\gamma_1$, $\gamma_2$ represent regularization parameters, and $D_1$, $D_2$, $D_3$, $D_4$, $D_5$, $D_6$ represent 6 diffusion tensors in different directions.

In one embodiment, R(•) constrains the sparsity of each diffusion tensor, or R(•) constrains a joint sparsity of the diffusion tensors.

In one embodiment, in the case that R(•) constrains the sparsity of each diffusion tensor, $$R(D) = \sum_{k=1}^{6} \|\Psi D_k\|_1;$$

in the case that R(•) constrains the joint sparsity of the diffusion tensors:

$$R(D) = \sum_i \sqrt{\sum_{k=1}^{6} \|\psi_i D_k\|_2^2},$$

wherein, $\Psi$ is an operator and represents sparse transform, $\psi_i$ represents the $i^{th}$ row of $\Psi$, $\|\cdot\|_1$ represents calculating L1 norm, and $\|\cdot\|_2$ represents calculating L2 norm.

The embodiments of the present application further provide an apparatus for denoising a magnetic resonance diffusion tensor, so as to solve the technical problem in the prior art of how to realize high precision denoising of diffusion tensor while not increasing scanning time and affecting spatial resolution, the apparatus includes:

a storage for storing instructions;
a processor which is coupled to the storage and is provided to execute the instructions stored in the storage, wherein the processor is provided for:
collecting data of K space;
calculating a maximum likelihood estimator of a diffusion tensor according to the collected data of K space;
calculating a maximum posterior probability estimator of the diffusion tensor by using sparsity of the diffusion tensor and sparsity of a diffusion parameter and taking the calculated maximum likelihood estimator as an initial value; and
calculating the diffusion parameter according to the calculated maximum posterior probability estimator.

In one embodiment, the processor is specifically used for calculating a maximum likelihood estimator of the diffusion tensor in accordance with the following formula:

$$\tilde{D} = \underset{D}{\operatorname{argmin}} \sum_m \left\| d_m - FI_0 e^{i\varphi_m} e^{-bg_m^T D g_m} \right\|_2^2$$

wherein, $\tilde{D}$ represents the maximum likelihood estimator of the diffusion tensor, $d_m$ represents data of K space corresponding to the $m^{th}$ diffusion weighted image, F represents Fourier coding matrix, $I_0$ represents a non-diffusion-weighted reference image, $\varphi_m$ represents a phase of the $m^{th}$ diffusion weighted image, b represents a diffusion weighted factor, and $g_m = (g_{xm}, g_{ym}, g_{zm})^T$ represents a diffusion gradient vector corresponding to the $m^{th}$ diffusion weighted image.

In one embodiment, the processor is specifically used for calculating a maximum posterior probability estimator of the diffusion tensor in accordance with the following formula:

$$\tilde{D} = \underset{D}{\operatorname{argmin}} \sum_m \left\| d_m - F_m I_0 e^{i\varphi_m} e^{-bg_m^T D g_m} \right\|_2^2 + \gamma_1 R(D) + \gamma_2 G(FA)$$

wherein, $$FA = \frac{\sqrt{2}}{2} \sqrt{3 - \frac{(D_1 + D_2 + D_3)^2}{D_1^2 + D_2^2 + D_3^2 + 2D_4^2 + 2D_5^2 + 2D_6^2}},$$

R(•) represents a penalty function acting on the diffusion tensor D, G(•) represents a penalty function acting on a diffusion parameter FA, $\gamma_1$, $\gamma_2$ represent regularization parameters, and $D_1$, $D_2$, $D_3$, $D_4$, $D_5$, $D_6$ represent 6 diffusion tensors in different directions.

In one embodiment, R(•) constrains the sparsity of each diffusion tensor, or R(•) constrains a joint sparsity of the diffusion tensors.

In one embodiment, in the case that R(•) constrains the sparsity of each diffusion tensor, $$R(D) = \sum_{k=1}^{6} \|\Psi D_k\|_1;$$

in the case that R(•) constrains the joint sparsity of the diffusion tensors:

$$R(D) = \sum_i \sqrt{\sum_{k=1}^{6} \|\psi_i D_k\|_2^2},$$

wherein, $\Psi$ is an operator and represents sparse transform, $\psi_i$ represents the $i^{th}$ row of $\Psi$, $\|\bullet\|_1$ represents calculating L1 norm, and $\|\bullet\|_2$ represents calculating L2 norm.

The embodiments of the present application further provide a computer program product for denoising a magnetic resonance diffusion tensor, including:

a computer readable storage medium having computer readable program codes implemented therein, the computer readable program codes include:

a computer readable program code configured to collect data of K space;

a computer readable program code configured to calculate a maximum likelihood estimator of a diffusion tensor according to the collected data of K space;

a computer readable program code configured to calculate a maximum posterior probability estimator of the diffusion tensor by using sparsity of the diffusion tensor and sparsity of a diffusion parameter and taking the calculated maximum likelihood estimator as an initial value; and a computer readable program code configured to calculate the diffusion parameter according to the calculated maximum posterior probability estimator.

In the embodiments of the present application, after data of K space is collected, a maximum likelihood estimator of the diffusion tensor is determined directly according to the data of K space, then a maximum posterior probability estimator of the diffusion tensor is calculated according to the calculated maximum likelihood estimator taken in conjunction with the sparsity of the diffusion tensor and the sparsity of the diffusion parameter, so as to determine the denoised diffusion tensor. This is different from a method of directly denoising a diffusion weighted image, as a result, it can avoid system errors introduced due to image denoising, solve the technical problem in the prior art of how to realize high precision denoising of diffusion tensor while not increasing scanning time and affecting spatial resolution, and effectively suppress noises in the diffusion tensor. Furthermore, because denoising is performed according to the sparsity of the diffusion tensor and the sparsity of the diffusion parameter, the estimation accuracy of the diffusion tensor is improved more effectively.

BRIEF DESCRIPTION OF DRAWINGS

In order to describe the technical solution in the embodiments of the present application more clearly, accompanying drawings required to be used in the description of the embodiments will be introduced briefly as follows. The accompanying drawings in the following description are merely some embodiments of the present application, and it is practicable for those skilled in the art to obtain other accompanying drawings according to these ones under the premise of making no creative efforts. In the drawings.

DESCRIPTION OF EMBODIMENTS

In order to make the purposes, technical solutions and advantages of the present application more clearly, the present application is further described in detail as follows in combination with embodiments and the accompanying drawings. Here, the schematic embodiments of the present application and description thereof are intended to explain the present application, but are not intended to limit the present application.

Figure 1:
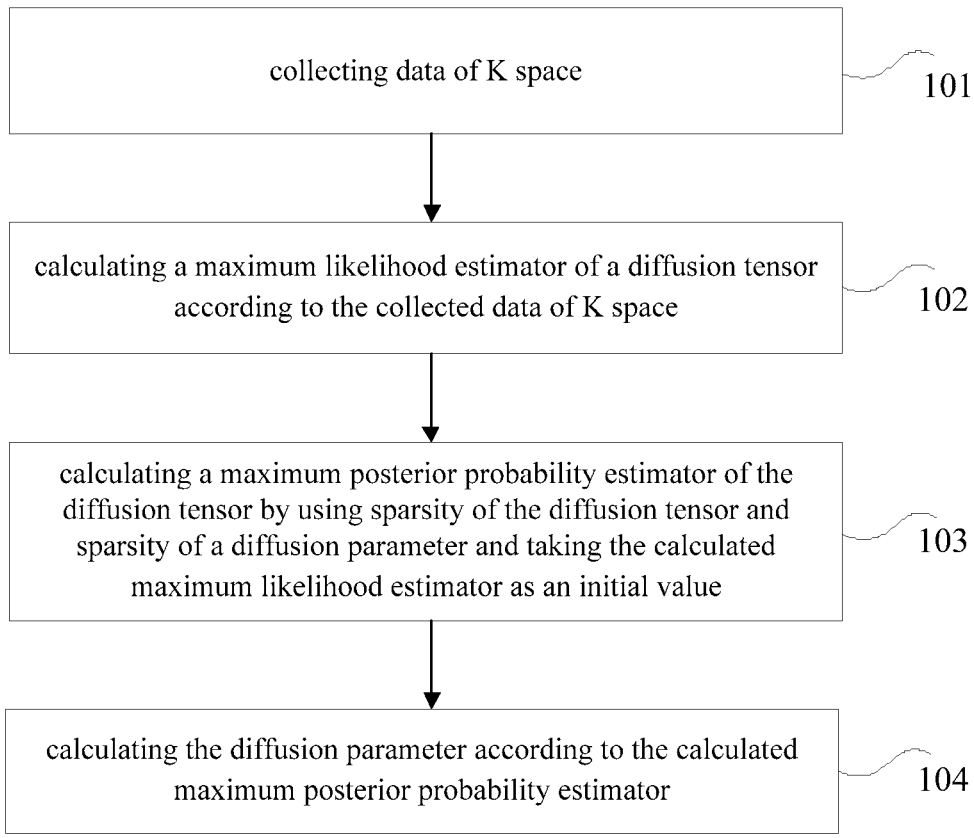
FIG. 1 is a flowchart of a method for denoising a magnetic resonance diffusion tensor according to an embodiment of the application.

The inventor has considered that, in the existing diffusion tensor imaging process, it is necessary to firstly obtain a diffusion weighted image, and then denoise the diffusion weighted image. In this way, however, system errors may be introduced, thereby leading to errors in final diffusion tensor estimation. Accordingly, there is provided in the embodiments with a method for denoising a magnetic resonance diffusion tensor. The method denoises a diffusion tensor directly by the acquired data of K space, without the need of calculating a diffusion weighted image or denoising the diffusion weighted image. As shown in FIG. 1, the method includes:

Step 101: collecting data of K space;

Step 102: calculating a maximum likelihood estimator of a diffusion tensor according to the collected data of K space;

Step 103: calculating a maximum posterior probability estimator of the diffusion tensor by using sparsity of the diffusion tensor and sparsity of a diffusion parameter and taking the calculated maximum likelihood estimator as an initial value; and Step 104: calculating the diffusion parameter according to the calculated maximum posterior probability estimator, wherein the diffusion parameter may include: MD, FA.

In the above embodiment, after the data of K space is collected, the maximum likelihood estimator of the diffusion tensor is determined directly according to the data of K space, then the maximum posterior probability estimator of the diffusion tensor is calculated by taking the calculated maximum likelihood estimator as an initial value taken in conjunction with the sparsity of the diffusion tensor and the sparsity of the diffusion parameter, so as to determine the denoised diffusion tensor. This is different from a method of denoising a diffusion weighted image, as a result, it can avoid system errors introduced due to image denoising, solve the technical problem in the prior art of how to realize high precision denoising of diffusion tensor while not increasing scanning time and affecting the spatial resolution, and effectively suppress noises in the diffusion tensor. Furthermore, because the denoising is performed according to the sparsity of the diffusion tensor and the sparsity of the diffusion parameter, the estimation accuracy of the diffusion tensor is improved more effectively.

Specifically, assuming that the sampled noises obey gaussian distribution, in combination with the above Formula 1 and Formula 2, the maximum likelihood estimator of the diffusion tensor may be written as:

$$\tilde{D} = \underset{D}{\mathrm{argmin}} \sum_m \left\| d_m - FI_0 e^{i\varphi_m} e^{-bg_m^T D g_m} \right\|_2^2$$

wherein, $\tilde{D}$ represents the maximum likelihood estimator of the diffusion tensor, $d_m$ represents data of K space corresponding to the $m^{th}$ diffusion weighted image, F represents Fourier coding matrix, $I_0$ represents a non-diffusion-weighted reference image, $\varphi_m$ represents a phase of the $m^{th}$ diffusion weighted image, b represents a diffusion weighted factor, and $g_m=(g_{xm}, g_{ym}, g_{zm})^T$ represents a diffusion gradient vector corresponding to the $m^{th}$ diffusion weighted image.

The maximum posterior probability estimator of the diffusion tensor may be calculated in accordance with the following formula:

$$\tilde{D} = \underset{D}{\mathrm{argmin}} \sum_m \left\| d_m - F_m I_0 e^{i\varphi_m} e^{-b g_m^T D g_m} \right\|_2^2 + \gamma_1 R(D) + \gamma_2 G(FA)$$

wherein, $$FA = \frac{\sqrt{2}}{2} \sqrt{3 - \frac{(D_1 + D_2 + D_3)^2}{D_1^2 + D_2^2 + D_3^2 + 2D_4^2 + 2D_5^2 + 2D_6^2}},$$

Accordingly, the above formula can be represented as:

$$\tilde{D} = \underset{D}{\mathrm{argmin}} \sum_m \left\| d_m - F_m I_0 e^{i\varphi_m} e^{-b g_m^T D g_m} \right\|_2^2 + \gamma_1 R(D) + $$

$$\gamma_2 G\left( \frac{\sqrt{2}}{2} \sqrt{3 - \frac{(D_1 + D_2 + D_3)^2}{D_1^2 + D_2^2 + D_3^2 + 2D_4^2 + 2D_5^2 + 2D_6^2}} \right)$$

wherein, R(•) represents a penalty function acting on the diffusion tensor D, G(•) represents a penalty function acting on the diffusion parameter, $\gamma_1$, $\gamma_2$ represent regularization parameters, and $D_1$, $D_2$, $D_3$, $D_4$, $D_5$, $D_6$ represent 6 diffusion tensors in different directions. Assuming that D and FA are both sparse, then it is practicable to let:

the penalty functions $$R(D) = \sum_{k=1}^{6} \|\Psi D_k\|_1$$

and G(•)=$\|\Psi(\bullet)\|_1$ constrain the sparsity of 6 diffusion tensors: ($D_1$, $D_2$, $D_3$, $D_4$, $D_5$, $D_6$) and the sparsity of the diffusion parameter FA, respectively, or, to let:

$$R(D) = \sum_i \sqrt{\sum_{k=1}^{6} \|\psi_i D_k\|_2^2}$$

constrain the joint sparsity of the diffusion tensors;

wherein, the operator $\Psi$ represents a sparse transform (for example, Wavelet transform and etc.), $\psi_i$ represents the $i^{th}$ row of $\Psi$, $\|\bullet\|_1$ represents calculating L1 norm, used for constraining the sparsity of the diffusion tensor in the sparse transform domain, and $\|\bullet\|_2$ represents calculating L2 norm.

In this way, the problem of denoising the diffusion tensor is equivalent to the problem of solving an optimal solution as described above. Specifically, a nonlinear conjugate gradient method may be used for solution solving.

That is, in the embodiment, by utilizing a diffusion tensor model and the inherent characteristics (e.g. sparsity) of the diffusion tensor and the diffusion parameter FA, the diffusion tensor is denoised directly by the acquired data of K space. The method skips steps of conventional image denoising, avoids errors of image denoising from affecting diffusion tensor estimation, thus can suppress noises in the diffusion tensor more effectively and improve the estimation accuracy of the diffusion tensor.

Figure 2:
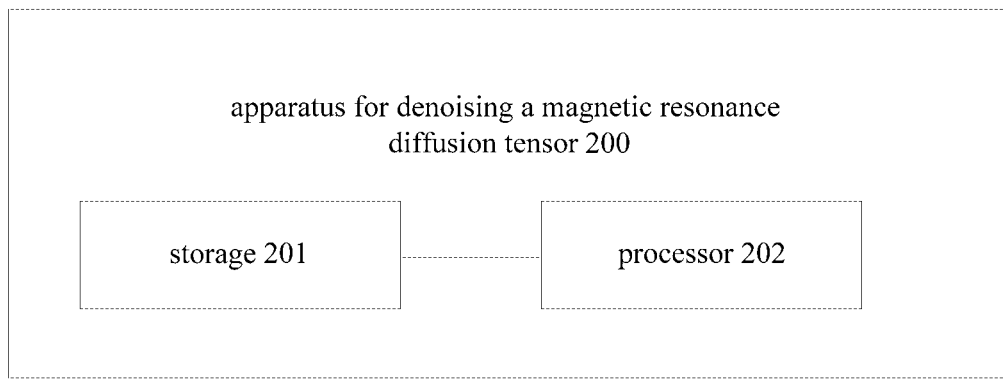
FIG. 2 is a structural block diagram of an apparatus for denoising a magnetic resonance diffusion tensor according to an embodiment of the application.

Based on the same inventive concept, the embodiments of the present application further provide an apparatus for denoising a magnetic resonance diffusion tensor, as described in the following embodiments. Because the principle for solving problems by the apparatus for denoising the magnetic resonance diffusion tensor is similar to that of the method for denoising the magnetic resonance diffusion tensor, the implementation of the apparatus for denoising the magnetic resonance diffusion tensor may refer to the implementation of the method for denoising the magnetic resonance diffusion tensor, thus repetitive parts will be omitted. As used below, the terms "unit" or "module" may realize combination of software and/or hardware with predetermined functions. Although the apparatus described in the following embodiments is preferably implemented by software, implementation through hardware or the combination of software and hardware may also be possible and conceivable. FIG. 2 is a structural block diagram of an apparatus 200 for denoising a magnetic resonance diffusion tensor according to an embodiment of the application. As shown in FIG. 2, the apparatus 200 includes: a storage 201 for storing instructions; a processor 202 which is coupled to the storage 201 and is provided to execute the instructions stored in the storage 201, wherein the processor 202 is provided for: collecting data of K space; calculating a maximum likelihood estimator of a diffusion tensor according to the collected data of K space; calculating a maximum posterior probability estimator of the diffusion tensor by using the sparsity of the diffusion tensor and the sparsity of a diffusion parameter and taking the calculated maximum likelihood estimator as an initial value; and calculating the diffusion parameter according to the calculated maximum posterior probability estimator.

In one embodiment, the processor 202 is specifically used for calculating the maximum likelihood estimator of the diffusion tensor in accordance with the following formula:

$$\tilde{D} = \underset{D}{\mathrm{argmin}} \sum_m \left\| d_m - FI_0 e^{i\varphi_m} e^{-b g_m^T D g_m} \right\|_2^2$$

wherein, $\tilde{D}$ represents the maximum likelihood estimator of the diffusion tensor, $d_m$ represents data of K space corresponding to the $m^{th}$ diffusion weighted image, F represents Fourier coding matrix, $I_0$ represents a non-diffusion-weighted reference image, $\varphi_m$ represents a phase of the $m^{th}$ diffusion weighted image, b represents a diffusion weighted factor, and $g_m=(g_{xm}, g_{ym}, g_{zm})^T$ represents a diffusion gradient vector corresponding to the $m^{th}$ diffusion weighted image.

In one embodiment, the processor 202 is specifically used for calculating the maximum posterior probability estimator of the diffusion tensor in accordance with the following formula:

$$\tilde{D} = \underset{D}{\operatorname{argmin}} \sum_m \left\| d_m - F_m I_0 e^{i\varphi_m} e^{-b g_m^T D g_m} \right\|_2^2 + \gamma_1 R(D) + \gamma_2 G(FA)$$

wherein, $$FA = \frac{\sqrt{2}}{2} \sqrt{3 - \frac{(D_1 + D_2 + D_3)^2}{D_1^2 + D_2^2 + D_3^2 + 2D_4^2 + 2D_5^2 + 2D_6^2}},$$

R(•) represents a penalty function acting on the diffusion tensor D, G(•) represents a penalty function acting on the diffusion parameter FA, $\gamma_1$, $\gamma_2$ represent regularization parameters, and $D_1$, $D_2$, $D_3$, $D_4$, $D_5$, $D_6$ represent 6 diffusion tensors in different directions.

In one embodiment, R(•) constrains the sparsity of each diffusion tensor, or R(•) constrains a joint sparsity of the diffusion tensors.

In one embodiment, in the case that R(•) constrains the sparsity of each diffusion tensor, $$R(D) = \sum_{k=1}^{6} \|\Psi D_k\|_1;$$

in the case that R(•) constrains the joint sparsity of the diffusion tensors:

$$R(D) = \sum_i \sqrt{\sum_{k=1}^{6} \|\psi_i D_k\|_2^2},$$

wherein, $\Psi$ is an operator and represents sparse transform, $\psi_i$ represents the $i^{th}$ row of $\Psi$, $\|\cdot\|_1$ represents calculating L1 norm, and $\|\cdot\|_2$ represents calculating L2 norm.

Figure 3:
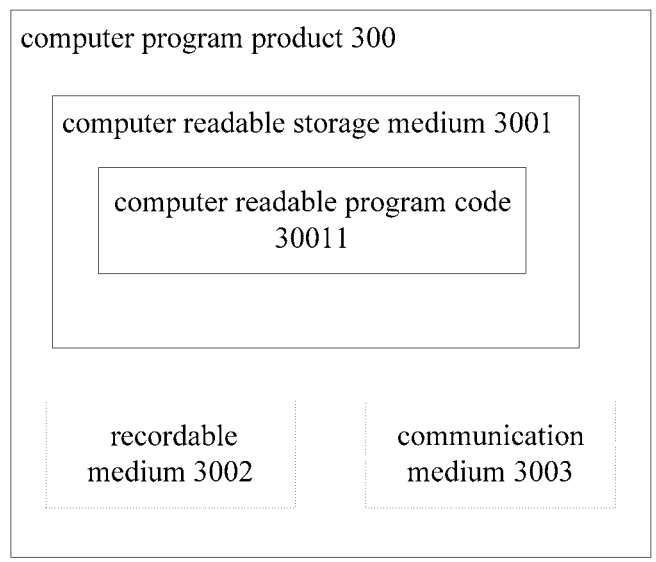
FIG. 3 is a schematic block diagram of a computer program product according to an embodiment of the application.

FIG. 3 is a block diagram showing an exemplary computer program product 300. In some examples, as shown in FIG. 3, the computer program product 300 includes a computer readable storage medium 3001 on which computer readable program codes 30011 implemented in the medium are stored, the computer readable program codes 30011 include: a computer readable program code configured to collect data of K space; a computer readable program code configured to calculate a maximum likelihood estimator of a diffusion tensor according to the collected data of K space; a computer readable program code configured to calculate a maximum posterior probability estimator of the diffusion tensor by using the sparsity of the diffusion tensor and the sparsity of a diffusion parameter and taking the calculated maximum likelihood estimator as an initial value; and a computer readable program code configured to calculate the diffusion parameter according to the calculated maximum posterior probability estimator.

It is also shown in FIG. 3 that, in some examples, the computer program product 300 may include one or more of a recordable medium 3002 and a communication medium 3003. The computer readable storage medium 3001 and the recordable medium 3002 may include (but are not limited to) floppy disks, hard disk drives (HDD), compact disks (CD), Digital Video Disks (DVD), digital tapes, computer storages and etc. The communication medium 3003 may include (but is not limited to) digital and/or analog communication medium (for example, fiber optic cables, waveguides, wired communication links, wireless communication links and etc.).

It can be seen from the above description that, the embodiments of the present application achieve the following technical effects: after data of K space is collected, the maximum likelihood estimator of the diffusion tensor is directly determined according to the data of K space, then the maximum posterior probability estimator of the diffusion tensor is calculated according to the calculated maximum likelihood estimator taken in conjunction with the sparsity of the diffusion tensor and the sparsity of a diffusion parameter, so as to determine the denoised diffusion tensor. This is different from a method of directly denoising a diffusion weighted image, as a result, it can avoid system errors introduced due to image denoising, solve the technical problem in the prior art of how to realize high precision denoising of a diffusion tensor while not increasing scanning time and affecting the spatial resolution, and effectively suppress noises in the diffusion tensor. Furthermore, because the denoising is performed according to the sparsity of the diffusion tensor and the sparsity of the diffusion parameter, the estimation accuracy of the diffusion tensor is improved more effectively.

Persons skilled in the art should appreciate that, the respective modules or the steps in the above mentioned embodiments of the present application can be implemented by using a universal computing device, they may be centralized on a single computing device or distributed on a network consisting of a plurality of computing devices, and alternatively, they may be implemented by using program codes that may be executed by computing devices, so that they may be stored in the storage device to be executed by computing devices, and in some circumstances, the steps as shown or described may be performed in an order different from that described herein, or they may be fabricated as various integrated circuit module, respectively, or multiple modules or steps therein may be fabricated as a single integrated circuit module. In this way, the embodiments of the present application are not limited to any specific combination of hardware and software.

The above are merely preferred embodiments of the present invention, and are not intended to limit the present invention. Various modifications and variations can be made to the embodiments of the present application for those skilled in the art. Any modifications, equivalent replacements, improvements and the like made within the spirit and principle of the present application shall be included within the protection scope of the present invention.

What is claimed is:

1. A method for demising a magnetic resonance diffusion tensor, comprising:
   collecting data of K space corresponding to a diffusion weighted image;
   calculating a maximum likelihood estimator of a diffusion tensor according to the collected data of K space;
   calculating a maximum posterior probability estimator of the diffusion tensor by using sparsity of the diffusion tensor and sparsity of a diffusion parameter and taking the calculated maximum likelihood estimator as an initial value; and
   calculating the diffusion parameter according to the calculated maximum posterior probability estimator to obtain a denoised magnetic resonance diffusion tensor.

2. The method according to claim 1, wherein the step of calculating a maximum likelihood estimator of the diffusion tensor according to the collected data of K space comprises:

calculating the maximum likelihood estimator of the diffusion tensor in accordance with the following formula:

$$\tilde{D} = \underset{D}{\mathrm{argmin}} \sum_m \left\| d_m - FI_0 e^{i\varphi_m} e^{-bg_m^T D g_m} \right\|_2^2$$

wherein, $\tilde{D}$ represents the maximum likelihood estimator of the diffusion tensor, $d_m$ represents data of K space corresponding to the $m^{th}$ diffusion weighted image, F represents Fourier coding matrix, $I_0$ represents a non-diffusion-weighted reference image, $\varphi_m$ represents a phase of the $m^{th}$ diffusion weighted image, b represents a diffusion weighted factor, and $g_m = (g_{xm}, g_{ym}, g_{zm})^T$ represents a diffusion gradient vector corresponding to the $m^{th}$ diffusion weighted image.

3. The method according to claim 2, wherein the step of calculating a maximum posterior probability estimator of the diffusion tensor by using sparsity of the diffusion tensor and sparsity of a diffusion parameter and taking the calculated maximum likelihood estimator as an initial value comprises:

calculating the maximum posterior probability estimator of the diffusion tensor in accordance with the following formula:

$$\tilde{D} = \underset{D}{\mathrm{argmin}} \sum_m \left\| d_m - F_m I_0 e^{i\varphi_m} e^{-bg_m^T D g_m} \right\|_2^2 + \gamma_1 R(D) + \gamma_2 G(FA)$$

wherein, $$FA = \frac{\sqrt{2}}{2} \sqrt{3 - \frac{(D_1 + D_2 + D_3)^2}{D_1^2 + D_2^2 + D_3^2 + 2D_4^2 + 2D_5^2 + 2D_6^2}},$$

R(•) represents a penalty function acting on the diffusion tensor D, G(•) represents a penalty function acting on the diffusion parameter FA, $\gamma_1$, $\gamma_2$ represent regularization parameters, and $D_1$, $D_2$, $D_3$, $D_4$, $D_5$, $D_6$ represent 6 diffusion tensors in different directions.

4. The method according to claim 3, wherein, R(•) constrains the sparsity of each diffusion tensor, or R(•) constrains a joint sparsity of the diffusion tensors.

5. The method according to claim 4, wherein,
in the case that R(•) constrains the sparsity of each diffusion tensor, $$R(D) = \sum_{k=1}^{6} \|\Psi D_k\|_1,$$

or in the case that R(•) constrains the joint sparsity of the diffusion tensors, $$R(D) = \sum_i \sqrt{\sum_{k=1}^{6} \|\psi_i D_k\|_2^2},$$

wherein, $\Psi$ is an operator and represents sparse transform, $\psi_i$ represents the ith row of $\Psi$, $\|\cdot\|_1$ represents calculating L1 norm, and $\|\cdot\|^2$ represents calculating L2 norm.

6. An apparatus for denoising a magnetic resonance diffusion tensor, comprising:
a storage for storing instructions;
a processor which is coupled to the storage and is provided to execute the instructions stored in the storage, wherein the processor is provided for:
collecting data of K space corresponding to a diffusion weighted image;
calculating a maximum likelihood estimator of a diffusion tensor according to the collected data of K space;
calculating a maximum posterior probability estimator of the diffusion tensor by using sparsity of the diffusion tensor and sparsity of a diffusion parameter and taking the calculated maximum likelihood estimator as an initial value; and
calculating the diffusion parameter according to the calculated maximum posterior probability estimator to obtain a denoised magnetic resonance diffusion tensor.

7. The apparatus according to claim 6, wherein, the processor is specifically used for calculating the maximum likelihood estimator of the diffusion tensor in accordance with the following formula:

$$\tilde{D} = \underset{D}{\mathrm{argmin}} \sum_m \left\| d_m - FI_0 e^{i\varphi_m} e^{-bg_m^T D g_m} \right\|_2^2$$

wherein, $\tilde{D}$ represents the maximum likelihood estimator of the diffusion tensor, $d_m$ represents data of K space corresponding to the $m^{th}$ diffusion weighted image, F represents Fourier coding matrix, $I_0$ represents a non-diffusion-weighted reference image, $\varphi_m$ represents a phase of the $m^{th}$ diffusion weighted image, b represents a diffusion weighted factor, and $g_m = (g_{xm}, g_{ym}, g_{zm})^T$ represents a diffusion gradient vector corresponding to the $m^{th}$ diffusion weighted image.

8. The apparatus according to claim 7, wherein, the processor is specifically used for calculating the maximum posterior probability estimator of the diffusion tensor in accordance with the following formula:

$$\tilde{D} = \underset{D}{\mathrm{argmin}} \sum_m \left\| d_m - F_m I_0 e^{i\varphi_m} e^{-bg_m^T D g_m} \right\|_2^2 + \gamma_1 R(D) + \gamma_2 G(FA)$$

wherein, $$FA = \frac{\sqrt{2}}{2} \sqrt{3 - \frac{(D_1 + D_2 + D_3)^2}{D_1^2 + D_2^2 + D_3^2 + 2D_4^2 + 2D_5^2 + 2D_6^2}},$$

R(•) represents a penalty function acting on the diffusion tensor D, G(•) represents a penalty function acting on the diffusion parameter FA, $\gamma_1$, $\gamma_2$ represent regularization parameters, and $D_1$, $D_2$, $D_3$, $D_4$, $D_5$, $D_6$ represent 6 diffusion tensors in different directions.

9. The apparatus according to claim 8, wherein, R(•) constrains the sparsity of each diffusion tensor, or R(•) constrains a joint sparsity of the diffusion tensors.

10. A non-transitory computer readable storage medium for denoising a magnetic resonance diffusion tensor, comprising:
computer readable program codes implemented therein, the computer readable program codes include:

a computer readable program code configured to collect data of K space corresponding to a diffusion weighted image;

a computer readable program code configured to calculate a maximum likelihood estimator of a diffusion tensor according to the collected data of K space;

a computer readable program code configured to calculate a maximum posterior probability estimator of the diffusion tensor by using sparsity of the diffusion tensor and a diffusion parameter and taking the calculated maximum likelihood estimator as an initial value; and a computer readable program code configured to calculate the diffusion parameter according to the calculated maximum posterior probability estimator to obtain a denoised magnetic resonance diffusion tensor.

* * * * *